US011470864B2

(12) United States Patent
Fourcassie et al.

(10) Patent No.: US 11,470,864 B2
(45) Date of Patent: Oct. 18, 2022

(54) MANUFACTURE OF A CEREAL-BASED LACTIC ACID-FERMENTED PRODUCT

(71) Applicant: DUPONT NUTRITION BIOSCIENCES APS, Copenhagen K (DK)

(72) Inventors: Pascal Fourcassie, Poitiers (FR); Claire Bonard, Chatellerault (FR); Veronique Laffitte, Dange-Saint-Romain (FR); Brett Wordon, Cape Town (ZA)

(73) Assignee: DUPONT NUTRITION BIOSCIENCES APS, Kongens Lyngby (DK)

( * ) Notice: Subject to any disclaimer, the term of this patent is extended or adjusted under 35 U.S.C. 154(b) by 492 days.

(21) Appl. No.: 16/092,091

(22) PCT Filed: Apr. 12, 2017

(86) PCT No.: PCT/EP2017/058744
§ 371 (c)(1),
(2) Date: Oct. 8, 2018

(87) PCT Pub. No.: WO2017/178514
PCT Pub. Date: Oct. 19, 2017

(65) Prior Publication Data
US 2019/0116849 A1  Apr. 25, 2019

(30) Foreign Application Priority Data

Apr. 13, 2016 (EP) .................................. 16165075
Apr. 13, 2016 (ZA) ................................ 2016/02520

(51) Int. Cl.
| | | |
|---|---|---|
| *A23L 7/104* | (2016.01) | |
| *C12N 1/20* | (2006.01) | |
| *C12R 1/225* | (2006.01) | |
| *C12R 1/25* | (2006.01) | |
| *C12R 1/46* | (2006.01) | |
| *A23C 11/10* | (2021.01) | |
| *A23L 2/38* | (2021.01) | |

(52) U.S. Cl.
CPC .............. *A23L 7/107* (2016.08); *A23C 11/10* (2013.01); *A23C 11/106* (2013.01); *A23L 2/38* (2013.01); *A23L 2/382* (2013.01); *A23L 7/104* (2016.08); *C12N 1/20* (2013.01); *C12N 1/205* (2021.05); *C12R 2001/225* (2021.05); *C12R 2001/25* (2021.05); *C12R 2001/46* (2021.05)

(58) Field of Classification Search
CPC ....... C12N 1/205; C12N 1/20; C12R 2001/225
See application file for complete search history.

(56) References Cited

U.S. PATENT DOCUMENTS 10,231,467 B2    3/2019  Tsuchimoto
2010/0098805 A1  4/2010  Vykhodtsev

FOREIGN PATENT DOCUMENTS

| CN | 101874546 A    | 11/2010 |
|---|---|---|
| FR | 2815830 A1     | 10/2000 |
| GB | 2092878 A      | 8/1982  |
| WO | 2014119343 A1  | 8/2014  |

OTHER PUBLICATIONS

English translation of CN 101874546 (Year: 2010).*
Sanni, A., Onilude, A. & Fatungase, M. Production of sour maize bread using starter-cultures. World Journal of Microbiology and Biotechnology 14, 101-106 (1998).*
Schweigart, et al., "The Production of Mahewu", National Nutrition Research Institute, R. Research Report No. 167, N.N.R.I. Bulletin No. 3 (1960).
Weiss, et al., "Lactobacillus lactis, Lactobacillus leichmannii and Lactobacillus bulgaricus, Subjective Synonyms of Lactobacillus delbrueckii, and Description of *Lactobacillus delbrueckii* subsp. *lactis* comb. nov. and *Lactobacillus delbrueckii* subsp. *bulgaricus* comb, nov.", System. Appl. Microbiol, vol. 4, pp. 552-557 (1983).
Schweigart, "The Drying of Lactic Acid Bacteria Cultures for Mahewu Production", LWT—Food Science and Technology, Academic Press, United Kingdom, vol. 4, No. 1, pp. 20-23 (1971).
Schweigart, "A study of fermentation in the production of Mahewu, an indigenous sour maize beverage of Southern Africa", Jahrgang vol. 18, No. 5, pp. 241-246 (1963).
Rogosa, et al., "Nomenclatural Considerations of Certain Species of Lactobacillus Beijernick", International J. Systematic Bacteiology, vol. 21, No. 2, pp. 177-186 (1971).
Nyanzi, "Phylogenetic analysis and possible practical applications of potentially probiotic Lactobacillus isolater", Tshwane University of Technology (2013).
Nyanzi, "Consumer acceptability of a symbiotic version of the maize beverage mageu", Dev. Southern Africa, vol. 27, No. 3, pp. 447-463 (2010).
Noort, "The Mahewu Industry" South African A Food Review, vol. 3, No. 5, pp. 129-133 (1978).
Search Report and Written Opinion for PCT/EP2017/058744 dated Aug. 2, 2017.
IPRP for PCT/EP2017/058744 dated Oct. 25, 2018.
Holzapfel, et al., "Industrialization of Mageu Fermentation in South Africa", In: KH Steinkraus, "Industrialization of Indigenous Food," pp. 363-407 (2004).
Database GNPD [Online], Mintel; "Strawberry Flavored Almond Non-Dairy Yogurt," XP002762665, database accession No. 2629931 (2014).
Database GNPD [Online], Mintel; "Plain Maize Drink," XP002762664, database accession No. 2858943 (2014).

(Continued)

*Primary Examiner* — Kade Ariani

(57) ABSTRACT

The present invention relates to a culture or kit-of-part comprising a *Lactobacillus delbrueckii* subsp *lactis* strain, and uses thereof to manufacture a cereal-based lactic acid-fermented product, in particular a maize-based lactic acid-fermented product such as mahewu.

3 Claims, 2 Drawing Sheets

Specification includes a Sequence Listing.

(56) References Cited

OTHER PUBLICATIONS

Database WPI; Thomson Scientific, London, GB; XP002762663 (2010).
Corrieu, "CINAC, System automatique de suivi des cultures", Janvier pp. 24-27 (1992).
Ayebo et al., "Fermentation of Maize-Based "Mahewu"", published in "Improving Young Child Feeding in Easter and Southern Africa", Proceedings of a workshop held in Nairobi, Kenya, Oct. 12-16, 1987, pp. 175-180.
Gadaga et al., "A review of traditional fermented foods and beverages of Zimbabwe", International Journal of Food Microbiology, vol. 53, 1999, pp. 1-11.
Salvador, "Development of Iron Fortified Cassava Mahewu", PhD thesis for University Pretoria, Jul. 2015, 160 pages.

\* cited by examiner

US 11,470,864 B2

MANUFACTURE OF A CEREAL-BASED LACTIC ACID-FERMENTED PRODUCT

CROSS-REFERENCE TO RELATED PATENT APPLICATIONS

This patent claims priority under 35 USC § 371 as a national phase of Int'l Patent Appl. PCT/EP2017/058744 (filed Apr. 12, 2017; and published Oct. 19, 2017 as Int'l Publ. No. WO2017/178514), which, in turn, claims priority to Europe Patent Application No. 16165075.9 (filed Apr. 13, 2016) and South Africa Patent Application No. 2016/02520 (filed Apr. 13, 2016). The entire text of each of the above-referenced patent applications is incorporated by reference into this patent.

FIELD OF THE INVENTION

The present invention relates to a culture or kit-of-part comprising a *Lactobacillus delbrueckii* subsp *lactis* strain, and uses thereof to manufacture a cereal-based lactic acid-fermented product, in particular a maize-based lactic acid-fermented product such as mahewu.

BACKGROUND OF THE INVENTION

Artisanal fermentation of cereal-based food products to make beverages (e.g. mahewu) relies on acidification by natural flora of the environment. Several lactic acid bacteria have been described in the literature and patents to be able to acidify efficiently maize-based substrate. Thus, the species *Lactobacillus plantarum* have been reported to be suitable for maize fermentation, after maize adaptation, in Nyanzy et al. 2010 [Development Southern Africa 27(3): 447] (see correction of species classification below and in FIGS. 1A and 1B) and in patent application FR2815830. The control bacterium C09, reported to be a *Lactobacillus delbrueckii* subsp *lactis* strain in Nyanzy et al. 2010, was further analyzed by 16SrDNA sequencing and reclassified as a *Lactobacillus plantarum* strain, as described in details in a presentation of Richard Nyanzi at the 20th Biennial International SAAFoST Congress and Exhibition in October 2013 (FIGS. 1A and 1B). *Lactobacillus delbrueckii* subsp *delbrueckii* and *delbrueckii* subsp *bulgaricus* subspecies have been mentioned to be used to acidify corn meal suspension in Schweigart 1960 [C.S.I.R. Research report No 167 (N.N.R.I. Bullletin No 3]. *Pediococcus* genus, in particular *P. acidilactici* species has been reported to be involved during fermentation of various cereal flours (maize, sorghum and millet) to produce non-alcoholic cereal-based foods in Franz 2014. In contrast to artisanal fermentation, industrial production of a cereal-based lactic acid-fermented product requires that a pH of 4.2 or lower be obtained in less than 20 h. Such a requirement is incompatible with for example the method reported in Schweigart 1960 [cited above] which involves adaptation of the strain to the cereal—via at least 12 sub-inoculations—before the production of the cereal-based lactic acid-fermented product.

There is therefore a need to simplify processes to manufacture cereal-based lactic acid-fermented product (e.g., by suppressing the step of adaptation of the microorganism to the cereal and/or by avoiding a previous propagation of the microorganism, before inoculation to the cereal-based suspension) while not compromising on reaching an acceptable pH (below 4.2) in an acceptable time (less than 20 h).

DESCRIPTION OF THE INVENTION

Figure 1A:
FIG. 1: A) program extract and abstract from Richard Nyanzi to the 20th Biennial International SAAFoST Congress and Exhibition, 7-10 Oct. 2013, CSIR International Convention Centre, Pretoria; B) front page and slide from Richard Nyanzi presentation to the 20th Biennial International SAAFoST Congress and Exhibition
Figure 1B:
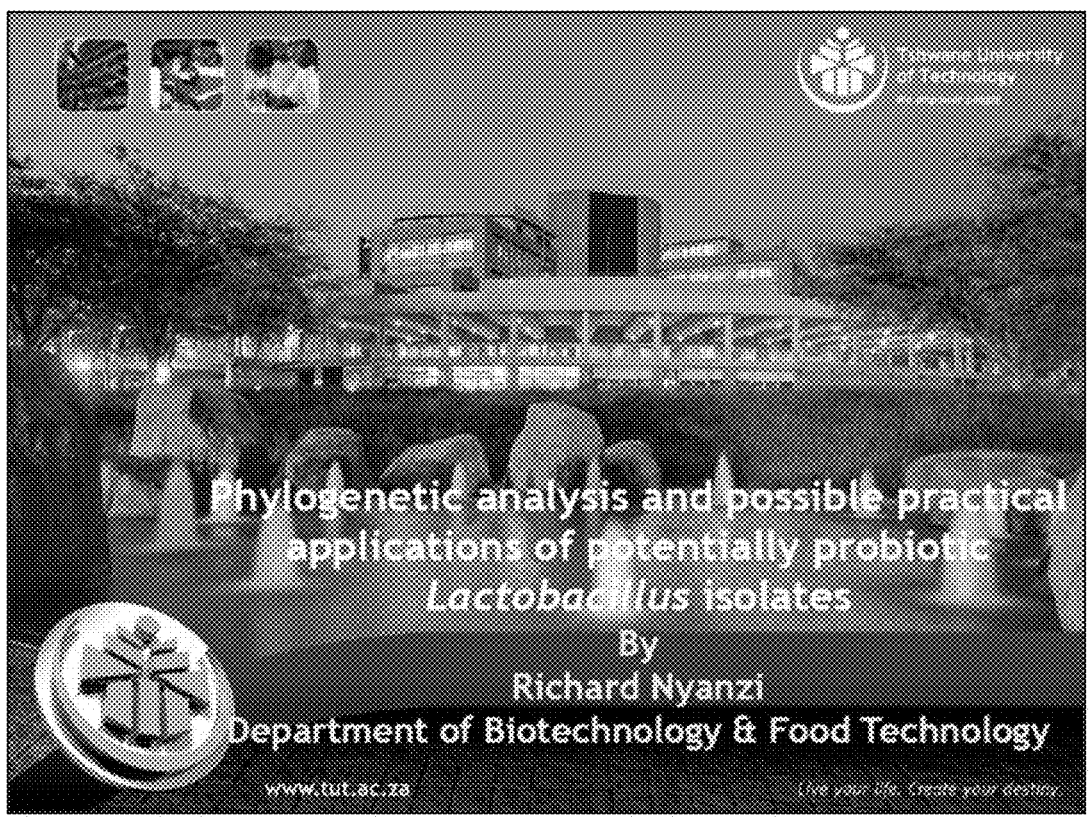

The inventors have surprisingly put in evidence that a *Lactobacillus delbrueckii* subsp *lactis* strain (known to be used in dairy applications, such as yoghurt and cheese) can be used to manufacture a cereal-based lactic acid-fermented product, in conditions acceptable for the industry. Indeed, a *Lactobacillus delbrueckii* subsp *lactis* strain—used alone or in combination with other microorganism(s)—has the ability to produce lactic acid on a cereal substrate, enabling to manufacture a cereal-based lactic acid-fermented product with an acceptable pH and in an acceptable time [for example, a product the pH of which is less or equals to 3.8, preferably less or equals to 3.6 or 3.5, in a fermentation time which is less than 20 h, more particularly less than 17 h].

Thus, the invention is directed to a method to produce a ready-to-eat cereal-based lactic acid-fermented product, comprising or consisting of:
  a) providing a cereal-based suspension containing an amount of cereal flour between 5 and 30% (w/w),
  b) adding at least one lactic acid bacterium to said cereal-based suspension; and
  c) incubating said lactic acid bacterium-added cereal-based suspension at an appropriate temperature, to obtain by lactic acid fermentation, a ready-to-eat cereal-based lactic acid-fermented product the pH of which is between 3 and 4.2;
  wherein said at least one lactic acid bacterium is a *Lactobacillus delbrueckii* subsp *lactis* strain.

Herein, the term "cereal-based suspension" is defined as commonly acknowledged in the art, i.e., a mixing of ground cereal grains/seeds in an aqueous medium, in particular in water. In a particular embodiment, the amount of cereal flour in the cereal-based suspension is comprised between 5 and 20%, in particular between 5 and 15% (w/w). In a particular embodiment, the amount of cereal flour in the cereal-based suspension is less than 10%, and in particular is between 5 and 10% (w/w). In a particular embodiment, the cereal of the cereal-based suspension, whatever the amount of flour defined herein, is selected from the group consisting of a cereal from the poaceae family and millet. In a particular embodiment, the cereal of the cereal-based suspension, whatever the amount of flour defined herein, is a cereal from the poaceae family. In a particular embodiment, the cereal-based suspension, whatever the amount of flour defined herein, is selected from the group consisting of a maize-, wheat-, millet-, barley-, fonio-, oat-, teff-, sorghum- and rye-based suspension. In a particular embodiment, the cereal-based suspension, whatever the amount of flour defined herein, is selected from the group consisting of a maize-, wheat-, millet-, barley-, fonio-, oat-, sorghum- and rye-based suspension. In a particular embodiment, the cereal of the cereal-based suspension, whatever the amount of flour defined herein, belongs to the poaceae family, and in particular is selected from the group consisting of maize, wheat, barley, fonio, oat, sorghum and rye. In a particular embodiment, the cereal-based suspension, whatever the amount of flour defined herein, is not an oat-based suspension. In a particular embodiment, the cereal-based suspension is selected from the group consisting of maize-, wheat-, fonio-, millet, sorghum- and rye-based suspension. In a particular embodiment, the cereal-based suspension is selected from the group consisting of maize-, wheat-, fonio-, millet and rye-based suspension. In a particular embodiment, the cereal-based suspension is a maize-based suspension.

The cereal-based suspension may also comprise additional ingredients—other than microorganisms —, such as sugar (e.g. glucose or saccharose), minerals (e.g., phosphate, calcium, magnesium, iron, zinc) or wheat bran. In a particular embodiment, the cereal-based suspension comprises sugar in a range between 1 and 2% (w/w). In a particular embodiment, there is no addition of sugar into the cereal-based suspension as defined herein and/or during the method to produce a ready-to-eat cereal-based lactic acid-fermented product. In a particular embodiment, the cereal-based suspension does not comprise dairy whey, such as lactose free whey, and/or milk or milk-based substrate and/or fat such as pork fat. Typically, the pH of a cereal-based suspension provided in step a) is comprised between 5 and 6.8, in particular between 5.5 and 6.8 [without being limited and as example only, here are the pH range obtained for the following cereal-based suspensions: maize: 5.7-6.3; wheat: 5.7-6.3; rye: 6-6.6; sorghum: 5.8-6.4; millet: 5.7-6.3; oat: 5.8-6.4; fonio: 5.7-6.3; rice: 6.2-6.8].

The term "adding" means put in contact the cereal-based suspension with at least a *Lactobacillus delbrueckii* subsp *lactis* strain as defined herein (i.e., a culture comprising or consisting of a *Lactobacillus delbrueckii* subsp *lactis* strain as defined herein). The term "adding" encompass the term "inoculating", i.e., that the addition of the *Lactobacillus delbrueckii* subsp *lactis* strain into the cereal-based suspension is done such that the *Lactobacillus delbrueckii* subsp *lactis* strain is able to be metabolically active, in order to produce lactic acid.

The at least *Lactobacillus delbrueckii* subsp *lactis* strain added in step b) of the present method is sufficient to produce a cereal-based lactic-acid fermented product from a cereal-based suspension, when added at appropriate level. In a particular embodiment, the at least *Lactobacillus delbrueckii* subsp *lactis* strain is added (inoculated) in step b), at a concentration of at least $10^5$ cfu (colony forming units) per g of cereal-based suspension. By "at least $10^5$ cfu/g of cereal-based suspension", it means at least $10^5$ cfu/g, at least $10^6$ cfu/g, at least $10^7$ cfu/g or at least $10^8$ cfu/g of cereal-based suspension. Any concentration expressed in "$10^x$ cfu/g" within this application is to be understood as $10^x \pm a$ half log of $10^x$ cfu/g (for example $10^5$ cfu/g means $10^5 \pm a$ half log of $10^5$, i.e. between $5.10^4$ and $5.10^5$ cfu/g).

The at least *Lactobacillus delbrueckii* subsp *lactis* strain can be added or inoculated under any form, such as under frozen, dried, freeze-dried, liquid or solid format, in the form of pellets or frozen pellets, or in a powder or dried powder. Thus, whatever the form, the concentration of the at least *Lactobacillus delbrueckii* subsp *lactis* strain is in the range of $10^5$ to $10^{12}$ cfu per g of culture, and more preferably at least $10^6$, at least $10^7$, at least $10^8$, at least $10^9$, at least $10^{10}$, at least $10^{11}$ or at least $10^{12}$ cfu/g of culture.

In an advantage of the invention, the at least *Lactobacillus delbrueckii* subsp *lactis* strain is directly added into the cereal-base suspension. By "directly added", it is meant that the *Lactobacillus delbrueckii* subsp *lactis* strain is added or inoculated into the cereal-based suspension without a previous adaptation to the cereal, part of the suspension and/or without a previous propagation.

In addition to the surprising finding that the *Lactobacillus delbrueckii* subsp *lactis* strain is able to use cereal as a substrate for lactic acid production, the inventors have also shown that this strain can be used without cereal adaptation, thus avoiding a long and complex adaptation process prior to the addition (inoculation) of this strain to the cereal-based suspension while at the same time still enabling the pH of cereal-based suspension to be decreased to acceptable level following lactic acid production (such as a pH less or equals to 3.8, preferably less or equals to 3.7, 3.6 or 3.5). Thus, in a particular embodiment, said at least *Lactobacillus delbrueckii* subsp *lactis* strain is directly added (inoculated) to said cereal-based suspension in step b) without previous adaptation to said cereal, i.e., that there is no step—before step b)—comprising one or more repeated sub-inoculation(s) or sub-culturing of the at least *Lactobacillus delbrueckii* subsp *lactis* strain in a medium comprising the cereal, part of the suspension. Thus, the method of the invention does not comprise an adaptation step to the cereal, part of the suspension before step b) or does not comprises one or more repeated sub-inoculation(s) or sub-culturing of the at least *Lactobacillus delbrueckii* subsp *lactis* strain in a medium comprising the cereal, part of the suspension before step b).

In a particular embodiment, possibly in combination with the embodiment on the absence of adaptation process, said at least *Lactobacillus delbrueckii* subsp *lactis* strain is directly added (inoculated) into the cereal-based suspension in step b) without previous propagation. The expression "directly added without previous propagation" encompasses both the inoculation of a frozen concentrate or dried concentrate of the at least *Lactobacillus delbrueckii* subsp *lactis* strain into the cereal-based suspension, and the inoculation of a frozen concentrate or dried concentrate of the at least *Lactobacillus delbrueckii* subsp *lactis* strain under a diluted form prior to inoculation (such as for example dilution of the concentrate(s) into water). In a particular embodiment, the at least *Lactobacillus delbrueckii* sub sp *lactis* strain is directly added or inoculated into the cereal-based suspension in a frozen format or as frozen pellets. In another embodiment of the invention, the at least *Lactobacillus delbrueckii* subsp *lactis* strain is directly added or inoculated into the cereal-based suspension under a powder form, such as a dried or freeze-dried powder. In another embodiment, the at least *Lactobacillus delbrueckii* subsp *lactis* strain is directly added or inoculated into the cereal-based suspension under a diluted form of frozen or dried concentrate of the at least *Lactobacillus delbrueckii* subsp *lactis* strain. Thus, the concentration of the frozen or dried concentrate as defined herein comprising or consisting of the at least *Lactobacillus delbrueckii* subsp *lactis* strain is in the range of $10^8$ to $10^{12}$ cfu per g of concentrate, and more preferably at least $10^8$, at least $10^9$, at least $10^{10}$, at least $10^{11}$ or at least $10^{12}$ cfu/g of concentrate. Together with the absence of adaptation process, the use of the at least *Lactobacillus delbrueckii* subsp *lactis* strain as a frozen or dried concentrate as defined herein has shown that it is advantageously possible to obtain a cereal-based lactic acid-fermented product, the pH of which is between 3 and 4.2, in a fermentation time which is less than 20 h, more particularly less than 17 h, at a fermentation temperature ranging between 42 and 47° C.

In a particular embodiment, the invention is directed to a method to produce a ready-to-eat cereal-based lactic acid-fermented product, comprising or consisting of:
  a) providing a cereal-based suspension containing an amount of cereal flour between 5 and 30% (w/w), preferably less than 10% (w/w);

b) directly adding at least one lactic acid bacterium to said cereal-based suspension; and c) incubating said lactic acid bacterium-added cereal-based suspension at an appropriate temperature, to obtain by lactic acid fermentation, a ready-to-eat cereal-based lactic acid-fermented product the pH of which is between 3 and 4.2;

wherein said at least one lactic acid bacterium is a *Lactobacillus delbrueckii* subsp *lactis* strain, and wherein said method does not comprise adaptation of said at least one *Lactobacillus delbrueckii* subsp *lactis* strain to said cereal prior to its addition and/or does not comprises previous propagation of said at least one *Lactobacillus delbrueckii* subsp *lactis* strain prior to its addition.

Any *Lactobacillus delbrueckii* subsp *lactis* strain can be used as long as the pH of the lactic-acid fermented cereal-based suspension obtained by the present method can reach a value between 3 and 4.2 after incubation. Thus, the *Lactobacillus delbrueckii* subsp *lactis* strain suitable for the invention is a strong acidifier on cereal substrate, i.e., is able to strongly reduce the pH of a cereal-based suspension as described herein.

For the avoidance of doubt, a *Lactobacillus delbrueckii* subsp *lactis* strain is defined herein as described in Weiss et al. 1983, System. Appl. Microbiol. 4, 552-557.

A *Lactobacillus delbrueckii* subsp *lactis* strain is considered to be "a strong acidifier on cereal substrate" when the pH value after 20 hours of fermentation according to assay A (described below) enables the maize-based suspension to reach a pH below 3.8. In a particular embodiment, a *Lactobacillus delbrueckii* subsp *lactis* strain tested by assay A and enabling the maize-based suspension to reach a pH below 3.7 or below 3.6 is preferred.

Assay A:

Maize meal (for example Maize meal Impala supplied by Premier Foods, Maxwell office Park, Magwa Crescent West, Waterfall City, 2090—South Africa) is thoroughly mixed with demineralized water at a ratio of 7% (W/W) of maize meal in a lab scale mixer device (for example Vowerk Thermomix TM31-1) to form a maize-based suspension. Dextrose is added at a concentration of 20 g/kg of the suspension during mixing step. Afterwards, the suspension is heat treated at 90° C.±3° C. during 90 min (±5 min) and then cooled down to the fermentation temperature. The tested *Lactobacillus delbrueckii* subsp *lactis* strain is directly inoculated at a rate of $10^6$ cfu/g of suspension (i.e., without previous adaptation to maize) either as a frozen concentrate or a dried concentrate [i.e., with a concentration of at least $10^8$ cfu per g of concentrate]. 80 ml (±5 ml) of suspension is then placed in flask of 100 ml equipped with a pH probe. The flask is displayed in a water bath thermo-regulated at a temperature of 47° C.±0.5° C. The pH evolution is measured with an online measurement system, Cinac system (CINAC, an automated system for control of lactic starters; Corrieu G. et al. Process Magazine; 1992, 1068; p. 24-2'7). The pH value after 20 hours of fermentation is measured and used to select *Lactobacillus delbrueckii* subsp *lactis* strain being strong acidifier on cereal substrate.

In an embodiment, the *Lactobacillus delbrueckii* subsp *lactis* strain added or inoculated in step b) of the method is the *Lactobacillus delbrueckii* subsp *lactis* strain deposited at the DSMZ under accession number DSM32049 on May 20, 2015.

In an embodiment, the *Lactobacillus delbrueckii* subsp *lactis* strain added or inoculated in step b) of the method is a variant of said DSM32049 strain, wherein said variant keeps the functionalities of the DSM32049 strain in terms of acidification properties, i.e., that the DSM32049 variant is a strong acidifier on cereal substrate when tested in assay A. A variant of said DSM32049 strain is a *Lactobacillus delbrueckii* subsp *lactis* strain which is a strong acidifier on cereal substrate when tested in assay A. A variant is herein defined as a *Lactobacillus delbrueckii* subsp *lactis* strain presenting at least one mutation, such as the addition, deletion, insertion and/or substitution of at least one nucleotide in its genome as compared to the DSM32049 strain. In a particular embodiment, the genome sequence of the variant has an identity of at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98%, or at least 99.99% to the genome sequence of the DSM32049 strain. Such a variant can be:

a natural variant obtained spontaneously from the DSM32049 strain after incubation in a selection medium. A natural variant is thus obtained without any genetic manipulation but only by natural mutation of the strain and selection of the strain in an appropriate medium; or a variant comprising at least one mutation in its genome, said mutation being induced by genetic engineering, for instance by directed mutagenesis or random mutagenesis. Random mutagenesis can be performed with UV radiations or mutagenic compounds such as nitrous acid, ethyl-methanesulfonate, NMethyl-N'-nitro-N-nitrosoguanidine, N-ethyl-N-nitrosourea, acridine orange, proflavine.

In an embodiment, the only microorganism added or inoculated into the cereal-based suspension is the *Lactobacillus delbrueckii* subsp *lactis* strain as defined herein (pure culture of *Lactobacillus delbrueckii* sub sp *lactis* strain).

In another embodiment, at least one additional microorganism(s), in particular 1, 2, 3, 4, 5 or 6 additional microorganism(s), is (are) added or inoculated together with the *Lactobacillus delbrueckii* subsp *lactis* strain into the cereal-based suspension. In a particular embodiment, the at least one additional microorganism added or inoculated together with said at least one *Lactobacillus delbrueckii* subsp *lactis* strain is not a *Bacillus subtilis* strain. In a particular embodiment, said at least one additional microorganism is a yeast or a bacterium. In a particular embodiment, said at least one additional microorganism is a lactic acid bacteria, in particular a lactic acid bacteria selected from the group consisting of *Streptococcus, Lactobacillus, Pediococcus, Lactococcus, Leuconostoc* and *Bifidobacterium* species. In a particular embodiment, the *Lactobacillus delbrueckii* subsp *lactis* strain as defined herein is added (inoculated) together with at least one, preferably one or two, *Streptococcus thermophilus* strain(s). In a particular embodiment, the at least one additional microorganism added or inoculated together with said at least one *Lactobacillus delbrueckii* subsp *lactis* strain is not a *Streptococcus thermophilus* strain or not a *Lactobacillus helveticus* strain. In a particular embodiment, the *Lactobacillus delbrueckii* subsp *lactis* strain as defined herein is added (inoculated) together with at least one, preferably one or two, protease-negative (prtS−) *Streptococcus thermophilus* strain(s). In an embodiment, the *Lactobacillus delbrueckii* subsp *lactis* strain as defined herein is added (inoculated) together with a second *Lactobacillus delbrueckii* subsp *lactis* strain, in particular a second *Lactobacillus delbrueckii* subsp *lactis* strain suitable for the invention as defined herein. In an embodiment, the *Lactobacillus delbrueckii* subsp *lactis* strain as defined herein is added (inoculated) together with at least one *Lactobacillus* species strain(s) other than a *Lactobacillus delbrueckii* subsp *lactis* strain, in particular with at least one *Lactobacillus* species strain(s) selected from the group consisting of *Lactobacillus plantarum*, *Lactobacillus delbrueckii* subsp *bulgaricus*, *Lactobacillus delbrueckii* subsp *helveticus* and any mixture of 2 or 3 of these *Lactobacillus* species strains. In a particular embodiment, the *Lactobacillus delbrueckii* subsp *lactis* strain as defined herein is added (inoculated) together with a *Lactobacillus plantarum* strain. In a particular embodiment, the *Lactobacillus delbrueckii* subsp *lactis* strain as defined herein is added (inoculated) together with a *Lactobacillus delbrueckii* subsp *bulgaricus* strain. In a particular embodiment, the *Lactobacillus delbrueckii* subsp *lactis* strain as defined herein is added (inoculated) together with a *Lactobacillus plantarum* strain and a *Lactobacillus delbrueckii* subsp *bulgaricus* strain. In a particular embodiment, said at least one additional microorganism is a propionic acid bacterium, in particular a *propionibacterium* strain.

The expression "together with" means that the *Lactobacillus delbrueckii* subsp *lactis* strain as defined herein and the at least one additional microorganism(s) can be added (inoculated) in step b) as separate cultures or as a mixture but both during step b). When the *Lactobacillus delbrueckii* subsp *lactis* strain and the at least one additional microorganism(s) are separated (for example as a kit of part), they can be added separately or simultaneously in time during the addition or inoculation step. The expression "as a mixture", means that the *Lactobacillus delbrueckii* subsp *lactis* strain and the at least one additional microorganism(s) is/are previously mixed to form a culture (or composition) before addition or inoculation. As a particular embodiment, such a mixture is a *Lactobacillus* strain culture consisting of a *Lactobacillus delbrueckii* subsp *lactis* strain as defined herein and at least one *Lactobacillus* species strain(s) other than a *Lactobacillus delbrueckii* subsp *lactis* strain, in particular at least one *Lactobacillus* species strain(s) selected from the group consisting of *Lactobacillus plantarum*, *Lactobacillus delbrueckii* subsp *bulgaricus*, *Lactobacillus delbrueckii* subsp *helveticus* and any mixture of 2 or 3 of these *Lactobacillus* species strains. In a particular embodiment, said *Lactobacillus* strain culture consists of thermophilic and mesophilic *Lactobacillus* strains.

Whatever the form, and either as a mixture or separate cultures, the concentration of the *Lactobacillus delbrueckii* sub sp *lactis* strain and the concentration of the at least one additional microorganism(s) are, each separately, in the range of $10^5$ to $10^{12}$ cfu per g of culture or mixture, and more preferably at least $10^6$, at least $10^7$, at least $10^8$, at least $10^9$, at least $10^{10}$, at least $10^{11}$ or at least $10^{12}$ cfu/g of culture or mixture. When in the form of a frozen or dried concentrate, the concentration of the *Lactobacillus delbrueckii* subsp *lactis* strain and the concentration of the at least one additional microorganism(s) are, each separately, in the range of $10^8$ to $10^{12}$ cfu/g of concentrate, and more preferably at least $10^8$, at least $10^9$, at least $10^{10}$, at least $10^{11}$ or at least $10^{12}$ cfu/g of concentrate.

"Incubating" means to maintain the cereal-based suspension previously inoculated with the at least *Lactobacillus delbrueckii* subsp *lactis* strain in appropriate conditions in order this strain produces lactic acid and thus decreases the pH of the cereal-based suspension, to obtain a cereal-based lactic acid-fermented product. The expression "by lactic acid fermentation" means that the fermentation (pH decrease) at step c) is mainly done by lactic acid production by at least the added *Lactobacillus delbrueckii* subsp *lactis* strain. In a particular embodiment, the fermentation does not encompass any alcoholic fermentation. In a particular embodiment, the fermentation is done only by lactic acid production. In an embodiment, the inoculated cereal-based suspension is incubated at a temperature ranging from 20 to 60° C., in particular between 30 and 50° C., more preferably between 40 and 50° C. or 42 and 47° C.

In an embodiment, the incubation lasts until the pH value of the cereal-based suspension decreases from an initial pH value comprised between 5 and 6.8, in particular between 5.5 and 6.8 to a pH value between 3 and 4.2, in particular between 3 and 4, in particular between 3.4 and 3.8, and preferably less or equals to 3.7 or 3.6, more preferably less or equals to 3.5. Typically, depending upon the temperature, the incubation lasts between 15 and 30 h, preferably between 15 and 20 h. In a particular embodiment of the invention, the incubation time to obtain a pH of 3.7 or 3.6 is less than 20 h, less than 19 h, less than 18 h, less than 17 h or less than 16 h (with in particular a minimal time of 10 h). In a particular embodiment, said time of incubation is determined for a fermentation temperature between 42 and 47° C.

The expression "cereal-based lactic acid-fermented" means a cereal-based suspension as defined herein whose pH has been decreased after fermentation and lactic acid production by at least the added *Lactobacillus delbrueckii* subsp *lactis* strain as defined herein. The pH of the ready-to-eat cereal-based lactic acid-fermented product obtained after lactic acid fermentation is comprised between 3 and 4.2, preferably between 3 and 4, preferably between 3.4 and 3.8, and preferably less or equals to 3.7 or 3.6, more preferably less or equals to 3.5. The expression "ready to eat" means that the product, such as the beverage, can be consumed as such, i.e., that the product does not need to be heated or cooked (e.g., fried, baked, steamed). In a particular embodiment, the ready-to-eat cereal-based lactic acid-fermented product as defined herein contains less than 0.5% (w/w) of alcohol content, in particular less than 0.25 or more particularly less than 0.1%. In a particular embodiment, the ready-to-eat cereal-based lactic acid-fermented product as defined herein contains less than 0.05% or less than 0.01% (w/w) of alcohol.

The cereal-based lactic acid-fermented product encompasses any food or feed product. In a particular embodiment, the cereal-based lactic acid-fermented product is under the form of a liquid and in particular is for human consumption (beverage).

In a particular embodiment, the ready-to-eat cereal-based lactic acid-fermented product the pH of which is between 3 and 4.2 is mahewu (also known as magou, mageu, amahewu or the like), a product based on a maize-based suspension. Thus, the invention is also directed to a method to produce mahewu, comprising:
 a) providing a maize-based suspension;
 b) optionally, heat-treating the suspension of step a) and cooling;
 c) adding at least one lactic acid bacterium to said suspension;
 d) incubating said mix at an appropriate temperature, to obtain mahewu;
wherein said at least one lactic acid bacterium is a *Lactobacillus delbrueckii* subsp *lactis* strain as defined herein.

In an embodiment of the method to produce mahewu, the incubation temperature is between 40 to 50° C., more particularly between 42 and 47° C.

In a particular embodiment of the method to produce mahewu, there is no addition of microorganisms other than lactic acid bacteria and in particular other than *Lactobacillus* species strains during the process. In a particular embodiment, there is no addition of α-amylase-containing composition during the method to produce mahewu. Indeed, the ability of *Lactobacillus delbrueckii* subsp *lactis* strain as defined herein to produce lactic acid on a cereal substrate enables to avoid the addition of enzyme(s) known to degrade polysaccharides such as starch.

The method of the invention can also optionally comprise filing a packaging with said lactic acid bacterium-added cereal-based suspension obtained in step b) before or during the incubation step or filing a packaging with the ready-to-eat cereal-based lactic acid-fermented product obtained in step c). Packaging for storage of ready-to-eat cereal-based lactic acid-fermented product can be any packaging designed to contain the cereal-based lactic acid-fermented product such as boxes, bottles, pouches. Typically, said packaging containing the cereal-based lactic acid-fermented product of the invention has a weight which is at least 100, 200, 300, 400 or 500 g. Typically, said packaging has a weight which is at least 500 g. In an embodiment, the weight of the packaging is 1 kg, 2 kg, 5 kg or 10 kg.

The invention is also directed to a ready-to-eat cereal-based lactic acid-fermented product, in particular mahewu, obtained or obtainable by a method as defined herein. Thus, the ready-to-eat cereal-based lactic acid-fermented product of the invention, in particular mahewu, is characterized in that:

it contains at least a *Lactobacillus delbrueckii* subsp *lactis* strain, optionally at a concentration comprised between $10^5$ to $10^8$ cfu/g, or at a concentration of at least $10^5$, at least $10^6$, at least 10' cfu/g of ready-to-eat cereal-based lactic acid-fermented product;

its pH is comprised between 3 and 4.2, in particular between 3.2 and 4, in particular between 3.5 and 3.8; and optionally, its alcohol content (w/w) is less than a value selected from 0.5, 0.25, 0.1, 0.05 and 0.01%.

The invention is also directed to a packaging as defined herein comprising a ready-to-eat cereal-based lactic acid-fermented product, in particular mahewu, obtained or obtainable by a method as described herein, or comprising a ready-to-eat cereal-based lactic acid-fermented product, in particular mahewu as defined herein.

The invention is also directed to a culture or kit-of-part comprising or consisting of a *Lactobacillus delbrueckii* subsp *lactis* strain. The definitions used within the method as far as they concern the *Lactobacillus delbrueckii* subsp *lactis* strain apply similarly for the culture or the kit-of-part. The culture or kit of part is suitable for the manufacture of a ready-to-eat cereal-based lactic acid-fermented product as described herein. Thus, the culture or kit of part of the invention comprises or consists of:

(a) a *Lactobacillus delbrueckii* subsp *lactis* strain which is a strong acidifier on cereal substrate when tested in assay A; and (b) at least one other microorganism, in particular 1, 2, 3, 4, 5 or 6 additional microorganism(s), wherein said at least one other microorganism(s) is(are) not microorganism(s) selected from the group consisting of a *Streptococcus thermophilus* strain, a *Lactobacillus helveticus* strain and a *Bacillus subtilis* strain.

In a particular embodiment, the at least one other microorganism can be a yeast or a bacteria. In a particular embodiment, the at least one other microorganism is a lactic acid bacteria, such as a lactic acid bacteria selected from the group consisting of a *Lactobacillus, Pediococcus, Lactococcus, Leuconostoc* and *Bifidobacterium* species. In a particular embodiment, the culture or kit of part comprises or consists of a) a *Lactobacillus delbrueckii* subsp *lactis* strain as described herein and b) at least one *Lactobacillus* species strain(s) other than a *Lactobacillus helveticus* strain. In a particular embodiment, the culture or kit of part as defined herein comprises or consists of thermophilic and mesophilic *Lactobacillus* strains. In a particular embodiment, the culture or kit of part comprises or consists of a) a *Lactobacillus delbrueckii* subsp *lactis* strain as described herein and b) at least one *Lactobacillus* species strain(s) selected from the group consisting of *Lactobacillus plantarum, Lactobacillus delbrueckii* subsp *bulgaricus* and a mixture thereof. In a particular embodiment, the at least one other microorganism is a propionic acid bacterium, in particular a *propionibacterium* strain.

In another embodiment, the invention is also directed to a culture or kit of part of the invention comprising or consisting of:

(a) a *Lactobacillus delbrueckii* subsp *lactis* strain which is a strong acidifier on cereal substrate when tested in assay A; and (b) a protease-negative (prtS−) *Streptococcus thermophilus* strain.

The expressions "protease positive" and "protease negative" (respectively prtS+ and prtS−), when applied to a *Streptococcus thermophilus* strain, mean respectively that this strain contains or does not contain the prtS gene. In a particular embodiment, a *Streptococcus thermophilus* strain is considered protease-positive (prtS+) when it gives a positive response by assay B. In a particular embodiment, a *Streptococcus thermophilus* strain is considered protease-negative (prtS−) when it gives a negative response by assay B.

Assay B:

In *Streptococcus thermophilus*, the presence of the prtS gene, which encodes a cell wall-anchored proteinase, can be detected by PCR using primer pair PrtSth-F as defined in SEQ ID NO:1 (5'-ggTTTCTgTTgTTAT-TgCAgC-3') and PrtSth-R as defined in SEQ ID NO:2 (5'-ATACCTgCACCTTgTTggCg-3'), providing an 897-bp amplicon. PCR amplification of this 897-bp internal fragment of the prtS gene is performed, using a standard thermal cycler (such as an Eppendorf Mastercycler) with a heated lid, in a total volume of 25 μL containing 5 μL of 5× Colorless GoTaq Flexi reaction buffer (Promega ref. M8305), 2.5 μL of MgCl2 25 mM (Promega ref. M8305), 0.25 μL of a dNTP mixture at 20 mM each (GE Healthcare Ref 28-4065-51), 0.25 μL of each primer at 20 approx. 100 ng of purified bacterial DNA, and 0.5 U of GoTaq Flexi DNA Polymerase (Promega ref. M8305). After an initial denaturation step of 5 minutes at 94° C., each of the 30 amplification cycles consist of denaturation at 94° C. for 30 s, primer annealing at 60° C. for 30 s, and primer extension at 72° C. for 1 min, and are followed by a final elongation step at 72° C. for 2 min. PCR products are visualized by electrophoresis on a 2% agarose gel using ethidium bromide staining. Presence of an 897-bp amplicon (positive result) means that the tested *Streptococcus thermophilus* is protease-positive. Absence of an 897- bp amplicon (negative result) means that the tested *Streptococcus thermophilus* is protease-negative.

The *Lactobacillus delbrueckii* subsp *lactis* strain and the at least one additional microorganism(s), or the *Lactobacillus delbrueckii* subsp *lactis* strain and the protease-negative (prtS−) *Streptococcus thermophilus* strain, either as a culture or as a kit-of-part, can be under any form suitable for addition or inoculation, in particular for direct addition or inoculation, into the cereal-based suspension, such as under frozen, dried, freeze-dried, liquid or solid format, in the form of pellets or frozen pellets, or in a powder or dried powder. In an advantage of the invention, the *Lactobacillus delbrueckii* subsp *lactis* strain and at least one additional microorganism(s), or the *Lactobacillus delbrueckii* subsp *lactis* strain and the protease-negative (prtS−) *Streptococcus thermophilus* strain, are in a frozen format or in the form of pellets or frozen pellets, in particular contained into one or more box or sachet. In another advantage of the invention, the *Lactobacillus delbrueckii* subsp *lactis* strain strain and at least one additional microorganism(s), or the *Lactobacillus delbrueckii* subsp *lactis* strain and the protease-negative (prtS−) *Streptococcus thermophilus* strain, are under a powder form, such as a dried or freeze-dried powder, in particular contained into one or more box or sachet.

In a particular embodiment, the *Lactobacillus delbrueckii* subsp *lactis* strain and at least one additional microorganism(s), or the *Lactobacillus delbrueckii* subsp *lactis* strain and the protease-negative (prtS−) *Streptococcus thermophilus* strain, either as a culture or as a kit-of-part, are in a concentration such that they can be directly added or inoculated into the cereal-based suspension without previous propagation, such as a frozen or dried concentrate.

Thus, whatever the form, the concentration of the *Lactobacillus delbrueckii* subsp *lactis* strain and the concentration of the at least one additional microorganism(s), or the concentration of the *Lactobacillus delbrueckii* subsp *lactis* strain and the concentration of the protease-negative (prtS−) *Streptococcus thermophilus* strain, are, each separately, in the range of $10^5$ to $10^{12}$ cfu per g of culture, and more preferably at least $10^6$, at least $10'$, at least $10^8$, at least $10^9$, at least $10^{10}$, at least $10^{11}$ or at least $10^{12}$ cfu/g of culture. When in the form of a frozen or dried concentrate, the concentration of the *Lactobacillus delbrueckii* sub sp *lactis* strain and the concentration of the at least one additional microorganism(s), or the concentration of the *Lactobacillus delbrueckii* subsp *lactis* strain and the concentration of the protease-negative (prtS−) *Streptococcus thermophilus* strain, are, each separately, in the range of $10^8$ to $10^{12}$ cfu/g of concentrate, and more preferably at least $10^8$, at least $10^9$, at least $10^{10}$, at least $10^{11}$ or at least $10^{12}$ cfu/g of concentrate.

The expression "A culture comprising or consisting of a *Lactobacillus delbrueckii* subsp *lactis* strain and at least one additional microorganism(s)" means that the *Lactobacillus delbrueckii* subsp *lactis* strain and the at least one additional microorganism(s) are physically mixed together. In an embodiment, the *Lactobacillus delbrueckii* subsp *lactis* strain and the at least one additional microorganism(s) are in the same box or in the same pouch. Similarly, the expression "A culture comprising or consisting of a *Lactobacillus delbrueckii* subsp *lactis* strain and a protease-negative (prtS) *Streptococcus thermophilus* strain" means that the *Lactobacillus delbrueckii* subsp *lactis* strain and the protease-negative (prtS−) *Streptococcus thermophilus* strain are physically mixed together. In an embodiment, the *Lactobacillus delbrueckii* sub sp *lactis* strain and the protease-negative (prtS−) *Streptococcus thermophilus* strain are in the same box or in the same pouch.

In contrast, the expression "A kit-of-part comprising or consisting of a *Lactobacillus delbrueckii* subsp *lactis* strain and at least one additional microorganism(s)" means that the *Lactobacillus delbrueckii* subsp *lactis* strain culture and the at least one additional microorganism(s) culture are physically separated but intended to be used together. Thus, the *Lactobacillus delbrueckii* subsp *lactis* strain and the at least one additional microorganism(s) are in different boxes or sachets. In an embodiment, the *Lactobacillus delbrueckii* subsp *lactis* strain and at least one additional microorganism (s) are under the same format, i.e., are in a frozen format, in the form of pellets or frozen pellets, a powder form, such as a dried or freeze-dried powder. Similarly, the expression "A kit-of-part comprising or consisting of a *Lactobacillus delbrueckii* subsp *lactis* strain and a protease-negative (prtS) *Streptococcus thermophilus* strain" means that the *Lactobacillus delbrueckii* sub sp *lactis* strain culture and the protease-negative (prtS−) *Streptococcus thermophilus* strain culture are physically separated but intended to be used together. Thus, the *Lactobacillus delbrueckii* subsp *lactis* strain and the protease-negative (prtS−) *Streptococcus thermophilus* strain are in different boxes or sachets. In an embodiment, the *Lactobacillus delbrueckii* subsp *lactis* strain and the protease-negative (prtS−) *Streptococcus thermophilus* strain are under the same format, i.e., are in a frozen format, in the form of pellets or frozen pellets, a powder form, such as a dried or freeze-dried powder.

In an embodiment, the *Lactobacillus delbrueckii* subsp *lactis* strain of the culture or kit-of-part is the *Lactobacillus delbrueckii* subsp *lactis* strain DGCC4550 deposited at the DSMZ under accession number DSM32049 on May 20, 2015 or a variant of said DSM32049 strain as defined herein.

In a particular embodiment, the culture as defined herein does not comprise ion chelator such as non-proteinasceous ion chelator.

The invention is also directed to the use of a *Lactobacillus delbrueckii* subsp *lactis* strain as defined herein, in particular the *Lactobacillus delbrueckii* subsp *lactis* strain DGCC4550 deposited at the DSMZ under accession number DSM32049 on May 20, 2015 or a variant thereof, or of a culture or kit-of-part as described herein, to manufacture a ready-to-eat cereal-based lactic acid-fermented product. In a particular embodiment, said strain or said variant is a strong acidifier on cereal substrate when tested in assay A.

DEPOSIT and EXPERT SOLUTION

The following deposit was made according to the Budapest treaty on the international recognition of the deposit of microorganisms for the purposes of patent procedure.

*Lactobacillus delbrueckii* subsp *lactis* strain deposited under accession number DSM32049 on May 20, 2015, at the DSMZ [Deutsche Sammlung von Mikroorganismen and Zellkulturen GmbH, Inhoffenstrasse 7B, D-38124 Braunschweig—Germany]. The DSM32049 *Lactobacillus delbrueckii* subsp *lactis* strain is from the DuPont/Danisco collection and was obtained from a fermented milk sample from Yugoslavia before 1990.

In respect to those designations in which a European Patent is sought, a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies (Rule 32 EPC).

EXPERIMENTAL

Example 1. Assay to Select Strains as Strong Acidifier on Cereal Substrate

Maize meal (for example Maize meal Impala supplied by Premier Foods, Maxwell office Park, Magwa Crescent West, Waterfall City, 2090—South Africa) was thoroughly mixed with demineralized water at a ratio of 7% (W/W) of maize meal in a lab scale mixer device (for example Vowerk Thermomix TM31-1) to form a maize-based suspension. Dextrose was added at a concentration of 20 g/kg of the suspension during mixing step. Afterwards, the suspension was heat treated at 90° C.±3° C. during 90 min (±5 min) and then cooled down to the fermentation temperature. The tested microorganism was directly inoculated at a rate of $10^6$ cfu/g of suspension (i.e., without previous adaptation to maize) as a frozen concentrate or a dried concentrate. 80 ml (±5 ml) of suspension was then placed in flask of 100 ml equipped with a pH probe. The flask was displayed in a water bath thermo-regulated at a temperature of 47° C.±0.5° C. when the microorganism belongs to the thermophilic lactic acid bacteria type or 30° C.±0.5° C. when the microorganism belongs to the mesophilic lactic acid bacteria type. The pH evolution was measured with an online measurement system, Cinac system (CINAC, an automated system for control of lactic starters; Corrieu G. et al. Process Magazine; 1992, 1068; p. 24-2'7). The pH value after 20 hours of fermentation (pH 20 h) is measured. A pH 20 h value below 3.8 was considered to select a strong acidifier strains on cereal substrate, and suitable for the manufacture of a ready-to-eat cereal-based lactic acid-fermented product according to the invention.

Example 2: Test of Species Known to be Involved in Maize Fermentation

Different strains reported to be involved in fermentation of maize (see background) were tested for their acidification properties on maize as described in example 1. These strains belong to the following species: *Lactobacillus delbrueckii bulgaricus*, *Lactobacillus delbrueckii delbrueckii*, *Pediococcus acidilactici* and *Lactobacillus plantarum*. DGCC numbers are internal references of the DuPont collection; DSM numbers and CNCM I numbers are the numbers assigned respectively by the Leibniz-Institut DSMZ-Deutsche Sammlung von Mikroorganismen und Zellkulturen and the Collection Nationale de Cultures de Microorganismes. Table 1 reports the pH after 20 h of fermentation for the different strains evaluated (each strain was tested 3 times, except strain DGCC9985 which was tested 6 times).

TABLE 1 pH results obtained with assay of example 1 on different strains known to be involved in maize suspension acidification

| | Tem- | | pH 20 h | |
| Strain | perature | n | average | Stdev |
| --- | --- | --- | --- | --- |
| Lb. delbrueckii bulgaricus (DGCC291) | 47° C. | 3 | 5.74 | 0.1 |
| Lb. delbrueckii bulgaricus (DGCC4078) | 47° C. | 3 | 4.43 | 0.06 |
| Lb. delbrueckii bulgaricus (DGCC4176) | 47° C. | 3 | 4.25 | 0.07 |
| Lb. delbrueckii delbrueckii (DGCC9985) | 47° C. | 6 | 4.63 | 0.03 |

TABLE 1-continued pH results obtained with assay of example 1 on different strains known to be involved in maize suspension acidification

| | Tem- | | pH 20 h | |
| Strain | perature | n | average | Stdev |
| --- | --- | --- | --- | --- |
| Pd. acidilactici (CNCM I-3113) | 47° C. | 3 | 5.29 | 0.02 |
| Pd. acidilactici (DGCC10368) | 47° C. | 3 | 5.46 | 0.08 |
| Lb. plantarum (DSM 22266) | 30° C. | 3 | 4.71 | 0.16 |
| Lb. plantarum (DGCC262) | 30° C. | 3 | 4.46 | 0.09 |
| Lb. plantarum (DGCC263) | 30° C. | 3 | 4.83 | 0.00 |

None of the tested strains fulfilled the requirements for selection according to the assay of example 1. Indeed, the pH at 20 h of fermentation was always far above 3.8. This showed that none of the species recognized of interest for maize suspension in the literature are suitable to be used for the manufacture a ready-to-eat cereal-based lactic acid-fermented product when directly inoculated to a cereal-based suspension (i.e., without previous adaptation to maize).

Example 3: Test of Species not Known to be Involved in Maize Fermentation

Several strains belonging to species not known to be involved in maize suspension acidification were tested for their acidification properties on maize as described in example 1. The fermentation temperature was 47° C. These strains belong to the following species: *Streptococcus thermophilus*, *Lactobacillus helveticus*, *Lactobacillus delbrueckii lactis*, *Lactobacillus delbrueckii sunkii* and *Lactobacillus delbrueckii jacobseni*. Table 2 reports the pH after 20 h of fermentation for the different strains evaluated (each strain has been tested 2 or 3 times).

TABLE 2 pH results obtained with the assay of example 1 on different strains not known to be involved in maize suspension acidification

| | | pH 20 h | |
| Strain | n | average | StDev |
| --- | --- | --- | --- |
| Streptococcus thermophilus (DGCC11393) | 3 | 5.51 | 0.14 |
| Streptococcus thermophilus (DGCC10856) | 3 | 5.04 | 0.26 |
| Streptococcus thermophilus (DGCC7766) | 3 | 5.85 | 0.06 |
| Streptococcus thermophilus (DGCC11043) | 3 | 5.73 | 0.02 |
| Streptococcus thermophilus (DGCC11138) | 3 | 4.40 | 0.01 |
| Lactobacillus helveticus (DGCC176) | 3 | 4.65 | 0.06 |
| Lactobacillus helveticus (DGCC1322) | 3 | 4.44 | 0.06 |
| Lactobacillus helveticus (DGCC192) | 3 | 4.86 | 0.22 |
| Lactobacillus helveticus (DGCC174) | 3 | 4.95 | 0.07 |
| Lactobacillus helveticus (DGCC4049) | 3 | 4.63 | 0.12 |
| Lactobacillus helveticus (DGCC4438) | 3 | 5.99 | 0.01 |
| Lactobacillus helveticus (DGCC4441) | 3 | 4.57 | 0.06 |
| Lactobacillus helveticus (DGCC4464) | 3 | 6.00 | 0.03 |
| Lactobacillus delbrueckii lactis (DSM 32049) | 3 | 3.55 | 0.15 |
| Lactobacillus delbrueckii lactis (DGCC4549) | 3 | 3.64 | 0.02 |
| Lactobacillus delbrueckii sunkii (DGCC12205) | 3 | 3.84 | 0.03 |
| Lactobacillus delbrueckii jacobsenii (DGCC12204) | 2 | 5.54 | 0.03 |

From the various tested species, it was surprisingly showed that only 1 species strictly fulfilled the requirements for selection according to the assay of example 1. Indeed, the pH at 20 h of fermentation was clearly below 3.8 for 2 *Lactobacillus delbrueckii lactis* strains, and in particular below 3.7 for one of these *Lactobacillus delbrueckii lactis* strains, and even below 3.6 for the other *Lactobacillus* delbrueckii lactis strain. This showed that the *Lactobacillus delbrueckii lactis* subspecies is suitable to be used for the manufacture of a ready-to-eat cereal-based lactic acid-fermented product when directly inoculated to a cereal-based suspension (i.e., without previous adaptation to maize). The *Lactobacillus delbrueckii lactis* DSM32049 strain showing a pH at 20 h below 3.6 was thus selected for further experiments.

Example 4: Assay of a *Lactobacillus delbrueckii* Subsp *Lactis* Strain in Various Cereal-Based Suspensions 4.1. Assay of *Lactobacillus delbrueckii* Subsp *Lactis* Strain DSM32049 on Wheat-Based, Millet-Based, Fonio-Based, Rye-Based and Oat-Based Suspension

*Lactobacillus delbrueckii* subsp *lactis* DSM 32049 strain was used in the fermentation of 5 different cereal-based suspensions [wheat, millet, fonio rye and oat]. The DSM 32049 strain was directly inoculated into the suspension, at a rate of $10^6$ cfu/g of suspension under frozen form, starting from a frozen concentrate at $1.4 \; 10^{10}$ cfu/g of culture. The experiments were performed by following the protocol described in example 1, with the following differences:
the maize meal has been replaced by wheat meal, millet meal, fonio meal, rye meal or oat meal;
dextrose was not added in the suspension; and
the fermentation temperature was adjusted at 45° C.

Table 3 reports the pH after 20 h of fermentation on these 4 cereal-based suspensions.

TABLE 3 pH after 20 h of fermentation at 45° C. obtained on different cereal suspensions using DSM32049

| Cereal | pH 20 h |
|---|---|
| wheat | 3.30 |
| millet | 3.76 |
| fonio | 3.91 |
| rye | 3.40 |
| oat | 4.1 |

This example shows that the *Lactobacillus delbrueckii* subsp *lactis* strain DSM 32049 not only is a strong acidifier on a maize substrate but also enables to acidify 4 other cereal-based suspensions to a pH below 4.2 after 20 h of fermentation, and even to a pH below 4.0 for fonio, to a pH below 3.8 for millet, to a pH of 3.4 for rye and to a pH of 3.3 for wheat.

4.2. Assay of *Lactobacillus delbrueckii* Subsp *Lactis* Strain DSM 32049 on Sorghum-Based and Rice-Based Suspension

*Lactobacillus delbrueckii* subsp *lactis* DSM 32049 strain has been used in the fermentation of 2 different cereal-based suspensions [sorghum and rice]. The DSM 32049 strain was directly inoculated into the suspension, at a rate of $10^6$ cfu/g suspension under frozen form, starting from a frozen concentrate at $1.4 \; 10^{10}$ cfu/g of culture The experiments were performed by following the protocol described in example 1, with the maize meal being replaced by sorghum meal or rice meal. Table 4 reports the pH after 20 h of fermentation on these 2 cereal-based suspensions.

TABLE 4 pH after 20 h of fermentation at 47° C. obtained on different cereal suspensions using DSM32049

| Cereal | pH 20 h |
|---|---|
| sorghum | 3.48 |
| rice | 3.93 |

This example shows that the *Lactobacillus delbrueckii* subsp *lactis* strain DSM 32049 also enables to acidify 2 other cereal-based suspensions to a pH below 4.0 after 20 h of fermentation, and even to a pH below 3.5 for rice, when supplemented with dextrose.

Conclusion

These two examples shows that strains of the *Lactobacillus delbrueckii* subsp *lactis* subspecies are suitable for the manufacture of a ready-to-eat cereal-based lactic acid-fermented product starting from various cereal-based suspensions, in particular at an industrial scale where direct inoculation of said strain into a cereal-based suspension is needed (i.e., without previous adaptation to the cereal).

Example 5: Assay of a *Lactobacillus delbrueckii* Subsp *Lactis* Strain in Combination with Other Strain(s) in Maize Flour The goal of this example was to determine that the co-inoculation of other strain(s) [in particular used for other functionalities than acidification] with a *Lactobacillus delbrueckii* subsp *lactis* strain, still enabled to obtain an acceptable pH at 20 h of fermentation.

*Lactobacillus delbrueckii* subsp *lactis* DSM 32049 strain was tested in co-inoculation with a strain selected among a *Lactobacillus plantarum* strain (2 different strains), a prtS-*Streptococcus thermophilus* strain (2 different strains) or a *Lactobacillus delbrueckii* subsp *bulgaricus* strain (3 different strains) [co-inoculations 1-21]. The *Lactobacillus delbrueckii* subsp *lactis* DSM 32049 strain was also tested in co-inoculation with both a *Lactobacillus plantarum* strain and a *Lactobacillus delbrueckii* subsp *bulgaricus* strain (2 combinations) [co-inoculations 22-28]. The same protocol as the one of example 1 was used, except that for each co-inoculation, several strains with different ratios have been tested. The different co-inoculations tested and the inoculation concentration (cfu/g of suspension) of each strain used is summarized in Table 5. Table 5 also specifies in which form (lyophilized [LYO] or frozen [FRO]) each strain was inoculated, as well as the initial concentration [Initial C°, in cfu/g of culture] of the used frozen or lyophilized concentrate.

For each co-inoculation, the following parameters were calculated and summarized in Table 6:
the pH after 20 h of fermentation (pH 20 h);
the time (in hours) to reach pH 3.8 (TpH 3.80); and
the time (in hours) to reach pH 3.6 (TpH 3.60).

TABLE 5 co-inoculations with DSM32049 and respective concentrations of each strain

| | Lactobacillus delbrueckii lactis (DSM 32049) | Lactobacillus plantarum (DGCC4715) | Lactobacillus plantarum (DGCC263) | Streptococcus thermophilus (CNCM I-3782) | Streptococcus thermophilus (DGCC7766) | L. delbrueckii bulgaricus (DGCC1261) | L. delbrueckii bulgaricus (DGCC3340) | L. delbrueckii bulgaricus (DGCC4176) |
|---|---|---|---|---|---|---|---|---|
| format | LYO | LYO | LYO | LYO | LYO | FRO | LYO | LYO |
| Initial C.° | $1.8 \cdot 10^{10}$ | $6.5 \cdot 10^{11}$ | $3.6 \cdot 10^{11}$ | $1.9 \cdot 10^{11}$ | $8.9 \cdot 10^{10}$ | $1.9 \cdot 10^{10}$ | $1.9 \cdot 10^{9}$ | $1.1 \cdot 10^{10}$ |
| 1 | $5 \cdot 10^5$ | $5 \cdot 10^5$ | | | | | | |
| 2 | $2 \cdot 10^5$ | $8 \cdot 10^5$ | | | | | | |
| 3 | $8 \cdot 10^5$ | $2 \cdot 10^5$ | | | | | | |
| 4 | $5 \cdot 10^5$ | | $5 \cdot 10^5$ | | | | | |
| 5 | $2 \cdot 10^5$ | | $8 \cdot 10^5$ | | | | | |
| 6 | $8 \cdot 10^5$ | | $2 \cdot 10^5$ | | | | | |
| 7 | $5 \cdot 10^5$ | | | $5 \cdot 10^5$ | | | | |
| 8 | $2 \cdot 10^5$ | | | $8 \cdot 10^5$ | | | | |
| 9 | $8 \cdot 10^5$ | | | $2 \cdot 10^5$ | | | | |
| 10 | $5 \cdot 10^5$ | | | | $5 \cdot 10^5$ | | | |
| 11 | $2 \cdot 10^5$ | | | | $8 \cdot 10^5$ | | | |
| 12 | $8 \cdot 10^5$ | | | | $2 \cdot 10^5$ | | | |
| 13 | $5 \cdot 10^5$ | | | | | $5 \cdot 10^5$ | | |
| 14 | $2 \cdot 10^5$ | | | | | $8 \cdot 10^5$ | | |
| 15 | $8 \cdot 10^5$ | | | | | $2 \cdot 10^5$ | | |
| 16 | $5 \cdot 10^5$ | | | | | | $5 \cdot 10^5$ | |
| 17 | $2 \cdot 10^5$ | | | | | | $8 \cdot 10^5$ | |
| 18 | $8 \cdot 10^5$ | | | | | | $2 \cdot 10^5$ | |
| 19 | $5 \cdot 10^5$ | | | | | | | $5 \cdot 10^5$ |
| 20 | $2 \cdot 10^5$ | | | | | | | $8 \cdot 10^5$ |
| 21 | $8 \cdot 10^5$ | | | | | | | $2 \cdot 10^5$ |
| 22 | $8 \cdot 10^5$ | $2 \cdot 10^5$ | | | | $1 \cdot 10^6$ | | |
| 23 | $8 \cdot 10^5$ | $2 \cdot 10^5$ | | | | $8 \cdot 10^5$ | | |
| 24 | $5 \cdot 10^5$ | $1.25 \cdot 10^5$ | | | | $3.75 \cdot 10^5$ | | |
| 25 | $4 \cdot 10^5$ | $2 \cdot 10^5$ | | | | $4 \cdot 10^5$ | | |
| 26 | $8 \cdot 10^5$ | $2 \cdot 10^5$ | | | | | | $1 \cdot 10^6$ |
| 27 | $8 \cdot 10^5$ | $2 \cdot 10^5$ | | | | | | $8 \cdot 10^5$ |
| 28 | $5 \cdot 10^5$ | $1.25 \cdot 10^5$ | | | | | | $3.75 \cdot 10^5$ |

TABLE 6 pH after 20 h of fermentation as well as times to reach pH 3.6 and 3.8 using different co-inoculations with DSM32049

| Composition | pH 20 h | TpH 3.80 (h) | TpH 3.60 (h) |
|---|---|---|---|
| 1 | 3.52 | 9.75 | 15.25 |
| 2 | 3.57 | 11.00 | 17.75 |
| 3 | 3.49 | 9.00 | 13.75 |
| 4 | 3.51 | 9.50 | 14.75 |
| 5 | 3.51 | 10.00 | 15.00 |
| 6 | 3.50 | 9.00 | 14.25 |
| 7 | 3.54 | 10.00 | 14.50 |
| 8 | 3.58 | 12.50 | 18.50 |
| 9 | 3.47 | 9.50 | 14.50 |
| 10 | 3.49 | 11.75 | 14.25 |
| 11 | 3.53 | 7.50 | 15.75 |
| 12 | 3.48 | 9.00 | 12.25 |
| 13 | 3.56 | 8.50 | 14.75 |
| 14 | 3.59 | 10.00 | 18.50 |
| 15 | 3.56 | 9.00 | 14.50 |
| 16 | 3.58 | 9.50 | 13.75 |
| 17 | 3.65 | 10.75 | >20 |
| 18 | 3.59 | 8.00 | 18 |
| 19 | 3.52 | 8.75 | 14.5 |
| 20 | 3.59 | 8.00 | 15.75 |
| 21 | 3.56 | 7.75 | 19 |
| 22 | 3.52 | 6.50 | 10.75 |
| 23 | 3.5 | 6.25 | 10.00 |
| 24 | 3.51 | 7.00 | 11.50 |
| 25 | 3.53 | 7.00 | 11.75 |
| 26 | 3.44 | 6.75 | 11.25 |
| 27 | 3.43 | 6.75 | 11.00 |
| 28 | 3.51 | 8.50 | 14.00 |

Conclusion

All the tested co-inoculations enabled to obtain a pH less than 3.7, 20 h after fermentation, i.e., 1 co-inoculation enabled to obtain a pH 20 h between 3.6 and 3.7, 19 co-inoculations a pH 20 h between 3.5 and 3.6 and 8 co-inoculations a pH 20 h equals to or below 3.5. Interestingly, the time to reach pH 3.6 was below 20 h for all, but one, co-inoculations and as short as 10 h (see #23).

The invention claimed is:

1. A culture or kit-of-part, suitable for the manufacture of a ready-to-eat cereal-based lactic acid-fermented product, wherein the culture or kit-of-part comprises:
   (a) a *Lactobacillus delbrueckii* subsp *lactis* strain which is a strong acidifier on cereal substrate when tested in assay A; and
   (b) at least one other microorganism, wherein the at least one other microorganism is at least one *Lactobacillus* species strain(s) selected from the group consisting of *Lactobacillus plantarum* and *Lactobacillus delbrueckii* subsp *bulgaricus*, a proprionibacterium, or a protease-negative (prtS-) *Streptococcus thermophilus* strain; and wherein the *Lactobacillus delbrueckii* subsp *lactis* strain and the at least one other microorganism are in frozen, dried, or freeze-dried form and are, each separately, at a concentration of at least $10^5$ cfu per g of culture.

2. The culture or kit-of-part according to claim 1, wherein: said *Lactobacillus delbrueckii* subsp *lactis* strain is the *Lactobacillus delbrueckii* subsp *lactis* strain DGCC4550 deposited at the DSMZ under accession number DSM32049 on May 20, 2015 or a variant of said DSM32049 strain, and said variant is a strong acidifier when tested in assay A.

3. The culture or kit-of-part according to claim 1, wherein the *Lactobacillus delbrueckii* subsp *lactis* strain and the at least one other microorganism are, each separately, at a concentration in the range of $10^5$ to $10^{12}$ cfu per g of culture.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 1
ggtttctgtt gttattgcag c                                              21

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 2
atacctgcac cttgttggcg                                                20
```